United States Patent [19]

Becker et al.

[11] Patent Number: 5,045,474

[45] Date of Patent: Sep. 3, 1991

[54] SEMI-AUTOMATIC PROCESS FOR WHITE CELL DIFFERENTIAL COUNT

[75] Inventors: Ruth M. Becker, Sunnyvale; Sherburne M. Edmondson, Jr., Cupertino, both of Calif.

[73] Assignee: Sequoia-Turner Corporation (Unipath), Mountain View, Calif.

[21] Appl. No.: 406,828

[22] Filed: Sep. 12, 1989

Related U.S. Application Data

[63] Continuation of Ser. No. 55,138, May 28, 1987, abandoned, which is a continuation of Ser. No. 805,971, Dec. 6, 1985, abandoned.

[51] Int. Cl.$^5$ .............................................. G01N 33/50
[52] U.S. Cl. ........................................ 436/63; 435/29; 435/34; 435/39
[58] Field of Search .................. 436/10, 17, 18, 63; 435/29, 34, 39

[56] References Cited

U.S. PATENT DOCUMENTS

| | | | |
|---|---|---|---|
| 3,874,852 | 4/1975 | Hamill | 436/63 |
| 4,099,917 | 7/1978 | Kim | 436/10 |
| 4,219,440 | 8/1980 | Runck et al. | 436/10 |
| 4,271,123 | 6/1981 | Curry et al. | 422/67 X |
| 4,286,963 | 9/1981 | Ledia et al. | 436/63 |
| 4,346,018 | 8/1982 | Carter et al. | 436/17 |
| 4,485,175 | 11/1984 | Ledis et al. | 436/63 |
| 4,493,821 | 1/1985 | Harrison | 436/17 X |
| 4,521,518 | 6/1985 | Carter et al. | 436/10 |
| 4,528,158 | 7/1985 | Gilles et al. | 436/54 X |
| 4,617,275 | 10/1986 | Matsuda et al. | 436/10 |

OTHER PUBLICATIONS

Davis et al., J. Med. Lab. Technol., vol. 26, pp. 26–30, 1969.
Bessman, Tex. Med., 80:33–35, 1984.
Dutcher, Lab. Med., vol. 14, No. 8, pp. 483–487, 1983.
Cox et al., A.J.C.P., pp. 297–305, 1985, Sep.
Coulter Electronics Marketing Memo, Jul., 1987, on "The Physician's Office Lab: How to Lessen Malpractice and Liability Risks", from Biby, Steve.

*Primary Examiner*—Robert J. Hill, Jr.
*Attorney, Agent, or Firm*—Limbach, Limbach & Sutton

[57] ABSTRACT

Hemotological analyses for hemoglobin and for three part white cell differential count. The dilution step is performed off line from the precisely controlled lysing and cell size measurement steps, thereby substantially reducing initial investment costs while retaining analytical accuracies. Simultaneous mixing means are provided for the lysing reagent addition step.

1 Claim, 3 Drawing Sheets

SEMI-AUTOMATIC PROCESS FOR WHITE CELL DIFFERENTIAL COUNT

This is a continuation of application Ser. No. 055,138, filed May 28, 1987, now abandoned, which is a continuation of application Ser. No. 805,971, filed Dec. 6, 1985, now abandoned.

TECHNICAL FIELD

This invention relates generally to methods and instrumentation for performing hematological analyses, and more particularly to an improved method for performing white cell differential counts on a semiautomated instrument.

BACKGROUND

The use of hematological analysis as a clinical tool for the recognition and treatment of various diseases has become more widespread due to the availability of automated instrumentation capable of economically performing this analysis. Since pathological changes can often be detected in the distributions of various blood cell subpopulations, hematological analyses can be used to detect diseases as well as to monitor therapies directed at the various diseases.

The relationship between the various hematological analyses and the particular application each variable has to malignant disease is described by Dr. David Bessman, MD, in "New Hematologic Indices: Use in Management of Malignant Diseases," Tex.Med. 80:33–35, 1984. For example, improved anemia classification is made possible by analyses of hemoglobin content, mean corpuscular volume(MCV) and red cell distribution width(RDW).

Leukocyte differentiation is also valuable in the detection of diseases and monitoring therapeutic effects. One valuable use, also reported in Dr. Bessman's article, is in outpatient chemotherapy, where drug administration depends in part on neutrophil and total white cell count. The differential may also be used to detect rare abnormalities, such as myelocytes or occasional blasts. A discussion of the unique problems associated with differentiating white cell subpopulations is presented in the detailed description of the invention below.

Comparisons have also been made between manually performed microscopic blood count determinations, and automated instrumentation for hematalogical analysis which mimics the visual smear technique. The results of these comparisons are compiled in Dutcher, Dr. Thomas F., "Automated Leukocyte Differentials: A Review and Prospectus," Lab. Med. 14: 483–487, 1983. Briefly, it has been reported: (1) The instruments are equal to or better than technologists with regard to precision (repeatability on the same specimen or same blood smear), especially in the classification of bands and monocytes. (2) The instruments are equal to or better than technologists with regard to accuracy, at least relative to finding abnormal cells (accuracy, as thought of in chemistry or even cell counting, is nearly impossible to assess in differential counting because of the inherent variability in 100- or 200-cell differentials). (3) The instruments produce results faster than technologists as timed from presentation of the slide to results available for reporting. (4) The instruments segregate smears into normal or abnormal (abnormal because of cell distribution outside normal range and the presence of abnormal cell types) as well as do technologists. The three part white cell differential instrumentation of the instant invention does not possess the same drawbacks as the instrumentation discussed in Dr. Dutcher's article. The reagents and cell size resistivity measurements of the present instrumentation provide greater accuracy than available in other automated instruments. This improvement in accuracy and levels of detectability, however, enhances the conclusions reached by Dr. Dutcher.

One of the most important criteria with respect to the purchase of such instrumentation has been cost. Dr. Dutcher's article reports that it is generally agreed that a daily workload of 250 to 300 or more differentials is required to justify the purchase on purely financial grounds. Although this number may vary somewhat for three-part differential instrumentation, it provides an order-of-magnitude estimate of the required throughput. Obviously, such a workload is atypical of a private practitioner's daily patient load. Consequently, hematological instrumentation has not become a standard of the private practitioner, but instead has been reserved for the clinical setting in which such workload thresholds can more easily be met. This invention, for the first time, makes economically possible the use of hematological instrumentation in the private practice without undue financial burdens on the practitioner or his/her patients. Previous investigators have discussed the need for providing a well-controlled lysing reaction, since white cell subpopulation enumeration and distribution is a complex function of cell lyse rates. It is reported, e.g., that accurate data can only be obtained if the lysing reagent addition step and transducer measurement step are precisely timed. See C. J. Cox et al., "Evaluation of Coulter Counter® S Plus IV" A.G.C.P. p.297, Sept., 1985. With this paramount design criterion in mind, it has been a common belief that white cell differentiation can only be accomplished on a fully automated instrument. Only in this manner can the precise timing required for this sensitive analysis be met. This invention recognizes, for the first time, that the timing of the dilution step is not as critical as the timing of the lysing reaction step and, therefore, the timing of this step does not have to be as precisely controlled. In this invention, once the dilution has been made off-line, either manually or semi-automatically, the diluted sample can be presented to the automatic instrument which introduces a carefully controlled volume of the lysing reagent at a precise rate and then measures and counts cell size. This modification of the dilution step, while reducing the complexity of the instrumentation, results in substantial savings in initial instrument costs, thereby making this semi-automatic hematological analyzer available to the office practitioner at a reasonable level of investment.

As discussed above, the use of platelet and red and white blood cell population distributions, and other physical characteristics of the various cells, to detect diseases at very early stages, or to monitor therapies for cancer and other disorders, greatly improves chances for satisfactory patient outcome. Making a hematological instrument available to the practitioner for use in his/her office places this line of detection at even earlier stages of patient screening. Thus, preventative measures can be taken more quickly and more effectively to treat detected diseases. The use of such instruments in the practitioner's office also makes the monitoring of chemotherapy much more convenient for the patient, minimizing the distances, expenses and waiting involved in the clinical setting.

Therefore, it is an object of this invention to provide a method for use with a low cost instrument for performing platelet and red and white blood cell analyses.

It is a further object of this invention to provide a method for use with an instrument which is capable of accurate platelet and red and white blood cell analyses and which is economically available for practitioners' use in the setting of their office.

It is still a further object of this invention to provide a method for use with instrumentation which will increase the availability of the valuable information derived from hematological data.

SUMMARY OF THE INVENTION

The improved process of the present invention permits off-line dilution of the blood sample prior to presentation to the automatic instrument which adds the lysing reagent in precisely controlled volumes and rates and then performs the desired measurements. The improved process provides mixing simultaneous to the addition of the lysing reagent when the diluted sample is presented to the automatic instrument. The simultaneous mixing feature, in conjunction with carefully controlled volumes and rates of lysing reagent addition, and precise timing of cell size measurement following lysing reagent addition, greatly improves the accuracy of the white cell differential results.

DETAILED DESCRIPTION OF THE INVENTION

Figure 1:
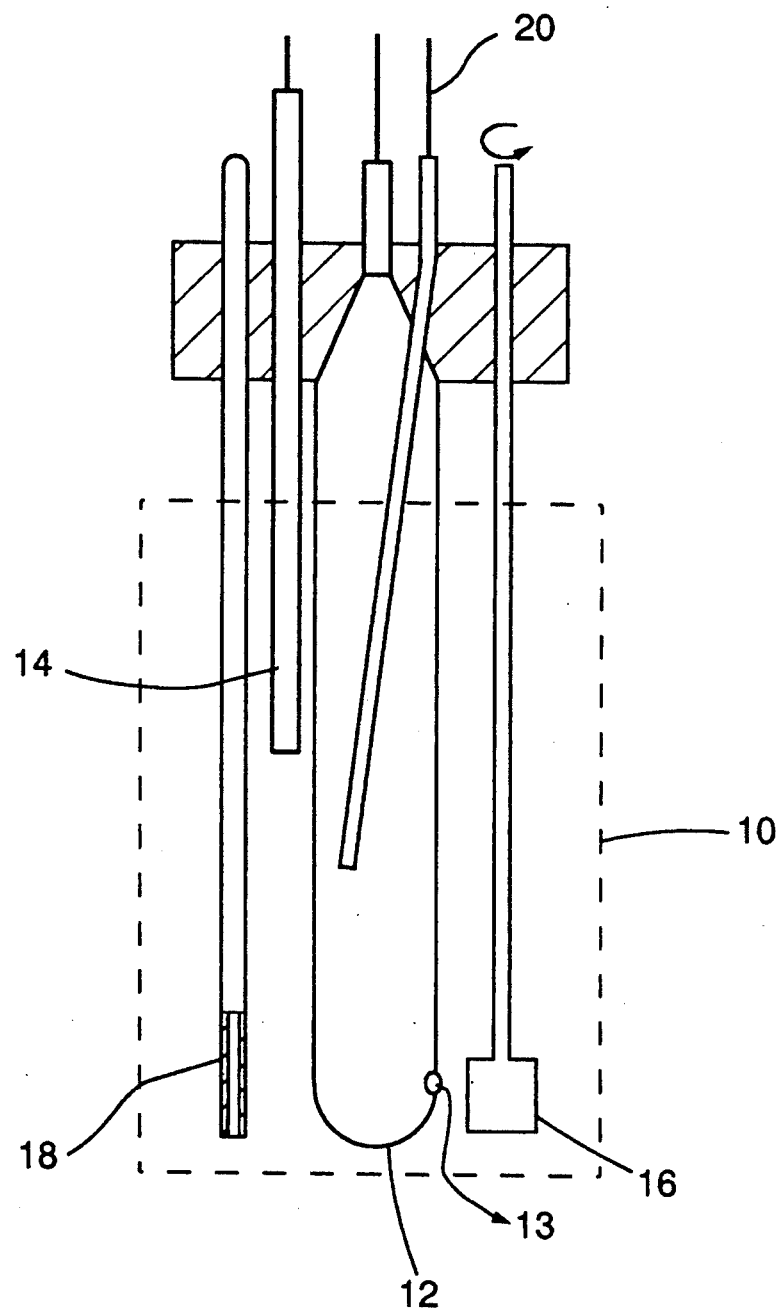
FIG. 1 is a detailed view of the lysing reagent mixing system.

In healthy man the circulating blood contains three major categories of cells: a population of small thrombocytes (or platelets) typically around 10 fl in average volume and around 150,000 to 400,000/ul in numerical concentration, the hemoglobin-carrying population of erythrocytes (or red cells) typically around 90 fl in average volume and around 4,000,000 to 6,000,000/ul in numerical concentration, and the population of larger nucleated leukocytes (or white cells). The leukocyte category consists of two numerically predominant or frequent subpopulations (the smaller monomorphonuclear lymphocytes and the larger polymorphonuclear neutrophilic granulocytes—each typically in the range of 1,000 to 5,000/ul in numerical concentration) and three infrequent subpopulations (the monomorphonuclear monocytes, the polymorphonuclear eosinophilic granulocytes and the polymorphonuclear basophilic granulocytes -each typically below 500/ul in numerical concentration).

Enumeration and distribution of the various blood subpopulations is achieved by lysing away all the extremely numerous and therefore obscuring erythrocytes (as is usual for resistivity leukocyte counting) and by simultaneously modifying the frequent (and also obscuring) lymphocyte and neutrophil subpopulations so that in terms of relative resistivity size, the lymphocytes are moved further below the infrequent subpopulation cells and the neutrophils are moved further above the infrequent subpopulation cells than are the native unmodified leukocytes of the circulating blood. In this way the two frequent leukocyte subpopulations are drawn apart to expose a clear stage on which pathophysiologic increases in any of the infrequent and rare subpopulations are readily apparent and can be evaluated quantitatively.

Simultaneous to the lysing and distribution of the white cell subpopulations, it is desirable to initiate the hemoglobin analysis as well as erythrocyte analysis. This concurrent analytical scheme reduces the total amount of whole blood sample necessary as well as the time involved for obtaining test results. Except for hemoglobin analysis, the various blood cell component analyses are dependent upon cell size as the measurable quantity. The lytic reaction is acutely time dependent. Therefore, in addition to carefully controlling the volume and rate of addition of lysing reagent, another component is required to affect cell size in solution for purposes of measurement. The reagent which is used to maintain cell size in solution is the diluent.

The ability to enumerate and to distribute the white cell subpopulations is a complex function of several lysing reaction rates. One of the reasons theorized for the accuracy of the current automated instrumentation versus microscopically observed smear techniques is the inherent ability of an automatic instrument to rigidly control reagent addition rates and volumes and reaction or "incubation" times. Thus, prior investigators laud full automation of sample handling, including both the dilution and lysing steps. While the perceived benefits of fully automated instrumentation have been widely accepted, the cost-benefit relationship of such a scheme has gone largely unnoticed. The hardware and software which are required to operate a fully automated process for hematological analysis have created a situation where the instrument purchase price can only be justified by performing several hundred analyses daily.

The present invention, for the first time in automated hematology, "de-automates" the dilution step, bringing it "off-line", contrary to the teachings of previous investigators, while retaining the critical timing mechanisms of the lysing reaction. The dilution step can be accomplished by either micropipetting or by commercially available automatic dilution instruments. The main focus of this invention is that the dilution occurs off-line from the lysing and measurement steps.

The present invention will be described with reference to the Sequoia-Turner Cell-Dyn ® 1500 (Sequoia-Turner Corp., Mountain View, Ca.) instrument, but it will be appreciated by those skilled in the art that the claimed improvements of the present invention are not intended to be limited to this particular embodiment.

In the improved process of the present invention, whole blood, in either 400 uL or 40 uL aliquots, is pre diluted using, e.g., automatic diluters such as the AD150, a product of Lab Status, Sweden, or the DD125, a product of Hook & Tucker, United Kingdom, or a disposable micropipette. One particularly preferred diluent, described in U.S. Pat. No. 4,745,071 comprises an aqueous solution of 1,3 dimethylurea, an organic buffer, 1-hydroxypyridene-2-thione, an inorganic salt to correct conductivity, ionic strength and osmolality, and sodium hydroxide. This diluent is most effective in unmasking the infrequent white cell sub-populations. Another diluent which may be used, described in U.S. Pat. No. 4,346,018, comprises an aqueous solution of procaine hydrochloride, N-(2-acetamido)iminidoacetic acid, chlorhexidene diacetate, dimethlylolurea, sodium sulfate and sodium chloride. The dilution rate is approximately 1:250, blood to diluent.

Referring now to FIG. 1, a cup 10 containing diluted blood is placed on the instrument in such a way that a measurement transducer 12, a lyse reagent tube 14 and a motor-driven mixing paddle 16 are all within the cup 10. When the instrument is activated by pressing a button to initiate processing, 1.25 ml of lyse reagent is added through tube 14 over a period of 2.5 seconds. Mixing is begun at the saxe time and continued for 2.5 seconds after all of the lyse reagent has been added. The reading of the sample, by passing it through an orifice 13 in the transducer 12, starts exactly twenty seconds after the beginning of the process. This scheme precisely controls lyse reaction time.

Also shown in FIG. 1 are additional features related to the automatic processing features of the instrument. An HGB tube 18 is used to aspirate an aliquot for hemoglobin analysis at a separate location in the instrument. A cleaning jet 20, positioned inside the measurement transducer 12, is used to introduce cleaning fluid, which in one particularly preferred embodiment is diluent, to the transducer 12 to remove blood cells from the interior of the transducer 12 before the introduction of a subsequent sample cup.

The lysing reagent used in the instant invention must be capable of categorizing the white cell population into three distinct subpopulations. One particularly preferred lysing reagent which meets this requirement is claimed in U.S. Pat. No. 4,745,071. The lysing reagent described therein comprises an aqueous solution of a single quaternary ammonium salt selected from the group consisting essentially of dodecyltrimethyl ammonium chloride, dodecyltrimethyl ammonium bromide, dodecyltrimethyl ammonium fluoride, dodecyltrimethyl ammonium sulfate, dodecyldimethylethyl ammonium chloride, dodecyldimethylethyl ammonium fluoride, dodecyldimethylethyl ammonium bromide, and dodecyldimethylethyl ammonium sulfate. Another suitable lysing reagent is described in U.S. Pat. No. 4,346,018 as an aqueous solution of quaternary ammonium salts such as hexadecyltrimethyl ammonium chloride, dodecyltrimethylammonium chloride, tetradecyltrimethylammonium bromide and mixtures thereof.

While the present invention describes a process for "deautomating" the dilution step, it is recognized that the critical kinetic requirements of white cell differentiation can only be met in an on-line, carefully-controlled automatic setting. The precision of the automated instrument is required to analyze the rare subpopulations of white cells which are often the most informative in terms of disease detection and therapy monitoring.

For the improved process of the instant invention to be viable from both technical and economic perspectives, it is important that the results obtained for the various blood component analyses be as good or better than the data obtained on the fully automated instruments currently available. To this end, correlation tests between the Cell-Dyn 1500 and the Coulter ® S Plus IV instrument were run.

Figure 2B:
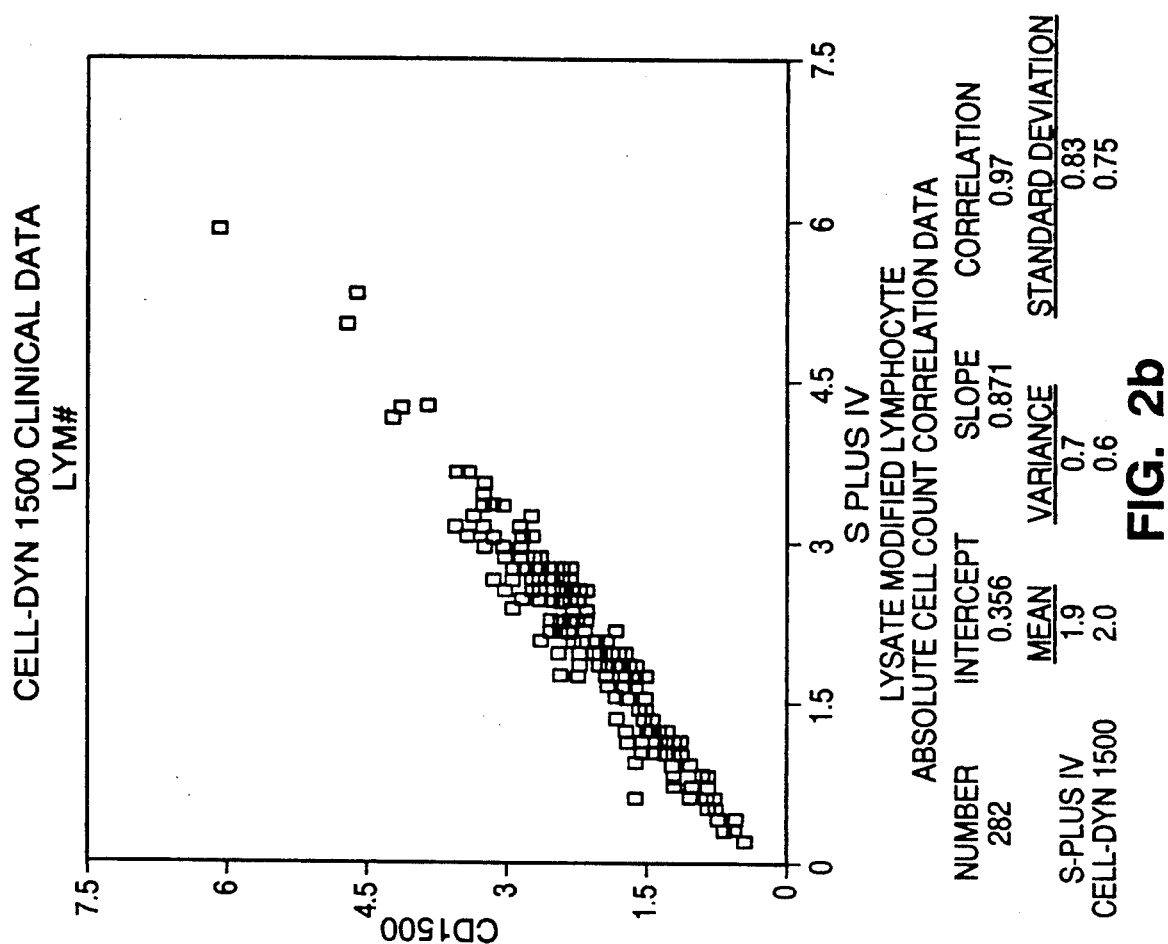
FIG. 2 contains two graphs (2a and 2b) showing the correlation between the instrumentation of the present invention and the fully automated Coulter ® Model S Plus IV.
Figure 2A:
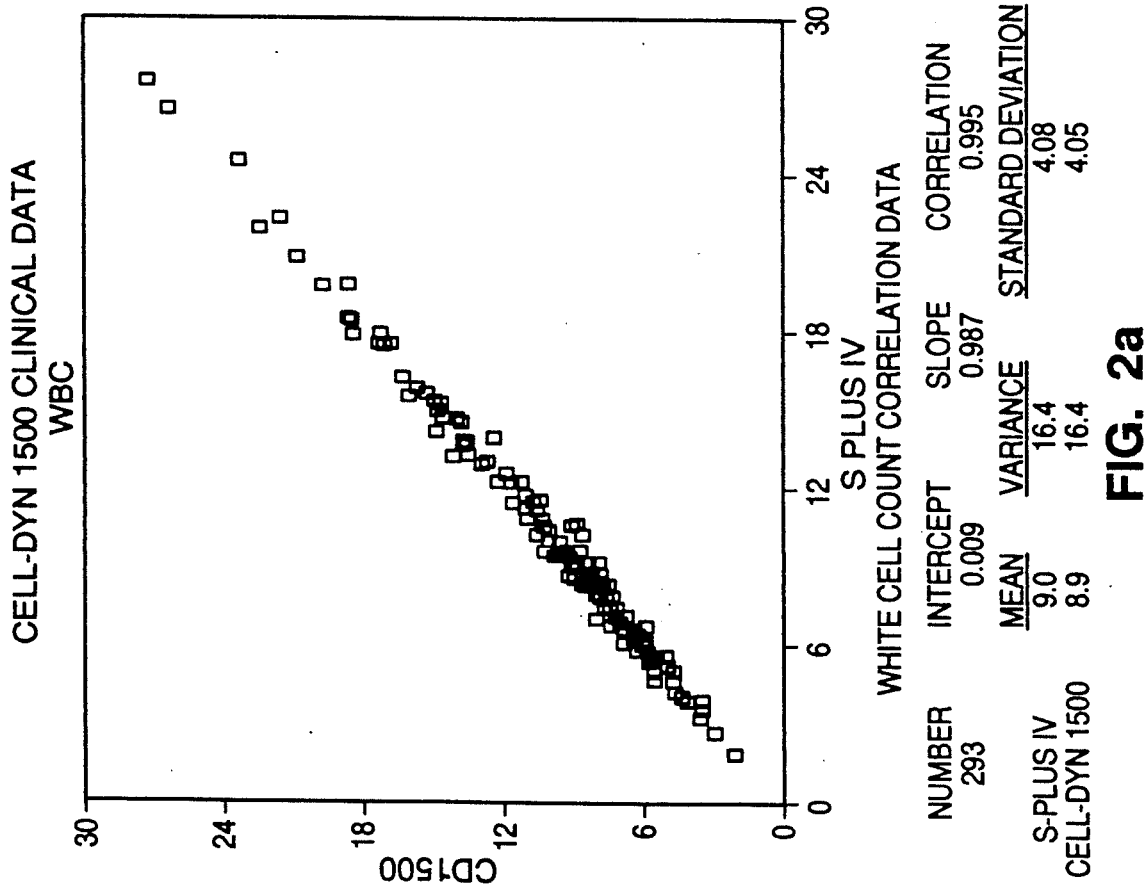
Figure 3B:
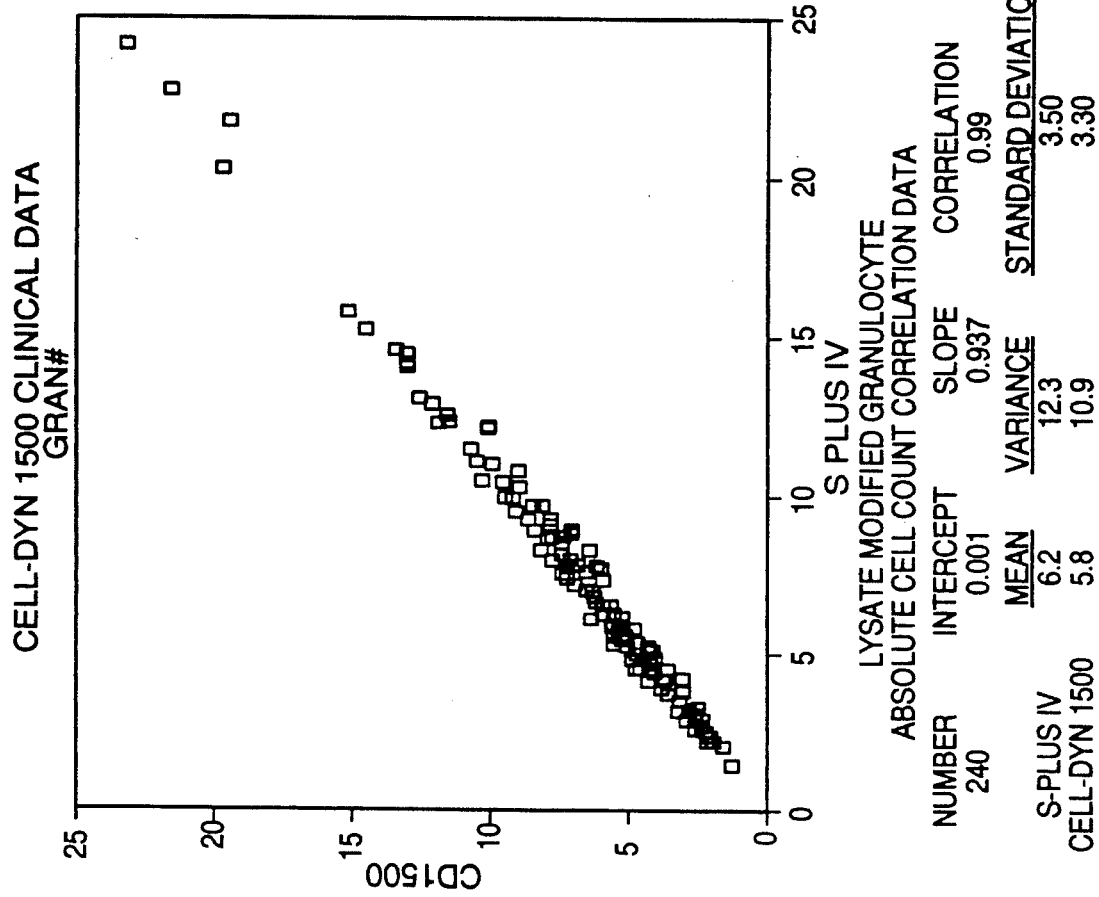
FIG. 3 contains two more graphs (3a and 3b) showing the correlation between the instrumentation of the present invention and the fully automated Coulter ® Model S Plus IV.
Figure 3A:
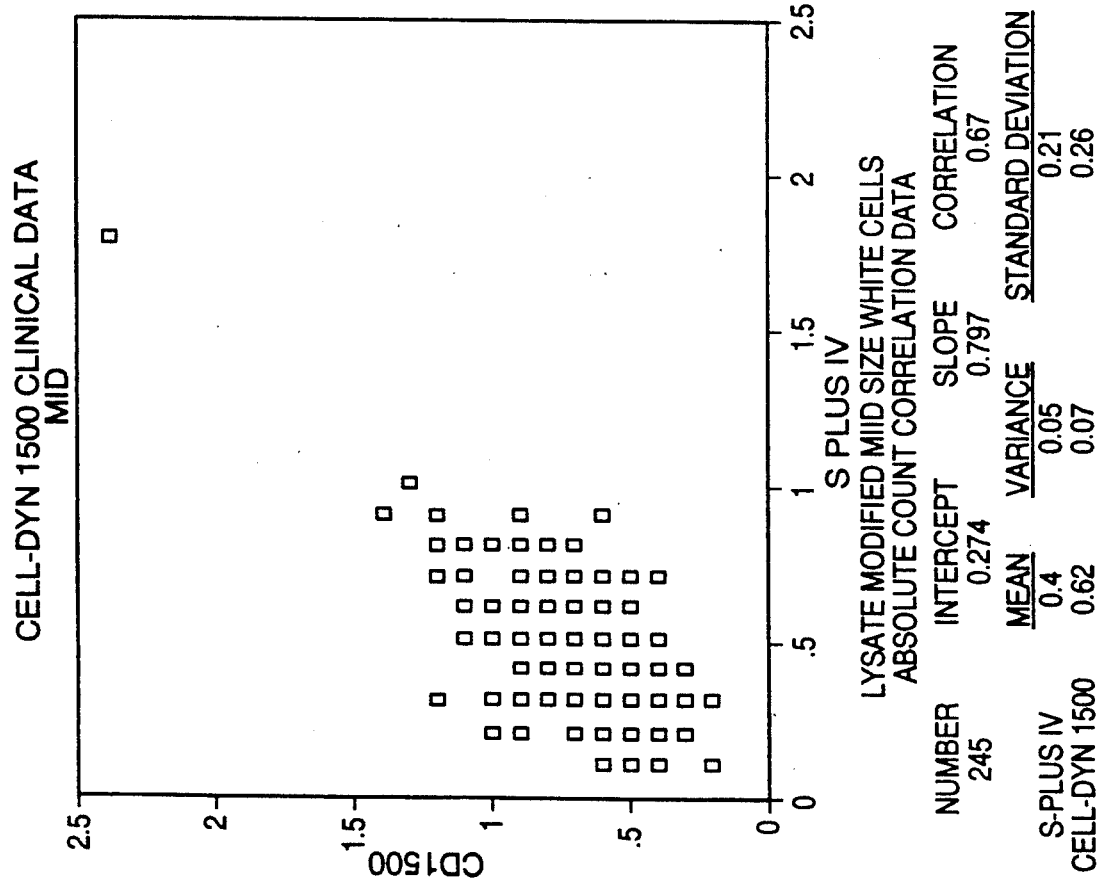

FIGS. 2 and 3 show data obtained on the Cell-Dyn 1500 unit compared with data obtained on the Coulter ® S Plus IV, a fully automated hematology analyzer. FIG. 3a shows that the white cell count data for both instruments correlates at a level of 99.5%.. FIG. 3b shows the correlation between the instruments to be at the 97% level for the measurement of lysate modified lymphocyte cells. FIG. 2a shows the correlation between instruments to be slightly lower, at a level of 67%, for measurement of mid size white cells. FIG. 2b indicates that the data for lysate modified granulocyte cell count correlates at a level of 99%. These correlations for the key measurements on each machine would suggest that no loss of accuracy occurs when the dilution of the whole blood sample is accomplished off line.

We claim:

1. In a process for hematological analysis, including three-part volumetric differential determination of white blood cell types, which consists essentially of the steps of:

a) contacting a whole blood sample with a diluent;

b) lysing red cells and partially lysing white cells in the diluted blood sample with a lysing reagent under precisely controlled time, mixing and volume conditions; and, c) obtaining a differentiation of partially lysed white cells in the diluted blood sample into distinct subpopulations by carefully timed resistivity measurements of cell size, the improvement wherein:

off-line diluter means are used to contact the whole blood sample with the diluent, and on-line means in an automatic instrument are provided to simultaneously mix the diluted blood sample while the lysing reagent is added thereto, said on-line mixing means comprising a motor-driven paddle which commences mixing of the diluted blood sample before the lysing reagent is added and which paddle continues to mix for a short interval after the lysing reagent has been added to the diluted blood sample, said resistivity measurements of cell size also being performed on-line in the automatic instrument and enabling a white cell differential determination by enumeration and distribution of partially lysed white cells into distinct subpopulations.

* * * * *